United States Patent [19]

Dewaele

[11] 4,144,249

[45] Mar. 13, 1979

[54] PREPARATION OF KETONE ACETALS

[75] Inventor: Silvain A. R. Dewaele, Evergem, Belgium

[73] Assignee: s.a. Texaco Belgium n.v., Brussels, Belgium

[21] Appl. No.: 852,391

[22] Filed: Nov. 17, 1977

Related U.S. Application Data

[62] Division of Ser. No. 689,776, Jun. 25, 1976, Pat. No. 4,092,331.

[30] Foreign Application Priority Data

Dec. 30, 1975 [GB] United Kingdom ............... 53095/75

[51] Int. Cl.$^2$ ........................................... C07D 317/44
[52] U.S. Cl. .............................. 260/340.5 R; 252/522; 424/282
[58] Field of Search .................................. 260/340.5 R

[56] References Cited

PUBLICATIONS

Dallacker et al., Justus Liebigs Annalen der Chemie, vol. 719, 1968, pp. 112–118.
Dallacker, Abstracts of Research Supported by the Petroleum Research Fund (196), p. 21.

Primary Examiner—Ethel G. Love
Attorney, Agent, or Firm—Thomas H. Whaley; Carl G. Ries; Carl G. Seutter

[57] ABSTRACT

Bisacetals can be prepared by reacting an acetal-forming compound, such as acetone or 2,2-dimethoxypropane, with an aromatic compound having two pairs of ortho- hydroxy groups, such as 1,2,4,5-tetrahydroxybenzene.

1 Claim, No Drawings

PREPARATION OF KETONE ACETALS

This is a division, of application Ser. No. 689,776, filed June 25, 1976, now U.S. Pat. No. 4,092,331.

Attempts to form acetals from polyhydric phenols with two or more pairs of ortho-positioned hydroxy groups have been less successful. Soloway in U.S. Pat. No. 2,927,096 describes the preparation of resins from aldehydes and polyhydric phenols, such as 1,2,4,5-tetrahydroxybenzene and pentahydroxy benzene. Dallacker et al in Annalen, Band 719 (1968), pp. 112–118 describe the preparation benzo [1.2-d:4.5-d']bis[1.3] dioxoles of the formula (III) wherein R is hydrogen, methoxy or allyl, by heating the corresponding mono-dioxole (IV) with chlorobromomethane in dimethyl formamide in the presence of potassium carbonate

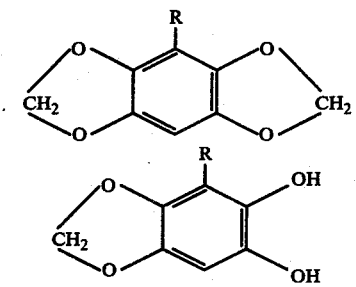

Kaye describes in the 13th Annual Report on Research, Petroleum Research Fund (1968) how reaction of catechol with cyclohexanone in the presence of toluene sulphonic acid in benzene gives only a 49% yield of the acetal, with some alkylation of the aromatic ring. Under the same conditions, no reaction took place between cyclohexanone and 1,2,4,5-tetrahydroxy-3,6-dimethylbenzene. He showed, however, in Abstracts of Research Supported by the Petroleum Research Fund (1968) p. 21 that 1,2,4,5-tetrahydroxy-3,5-dimethylbenzene formed an acetal (V) when heated with dichlorodiphenyl methane.

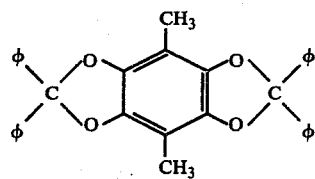

The object of the present invention is the preparation of ketone acetals from polyhydric phenols having at least two pairs of hydroxy groups in ortho-positions.

A further object of the present invention is the preparation of such acetals by a simple one-step reaction.

SUMMARY OF THE INVENTION

The present invention provides a process for the preparation of ketone acetals from polyhydric phenols containing at least two pairs of hydroxy groups in ortho-positions which comprises reacting a polyhydric phenol having at least four OH groups including at least two pairs of OH groups in ortho-positions with a ketone, or a dialkyl acetal of such a ketone, in the presence of a mon-aqueous solvent and a strong Lewis acid catalyst.

DESCRIPTION OF SPECIFIC EMBODIMENTS

Preferably, the polyhydric phenol is a compound of the formula

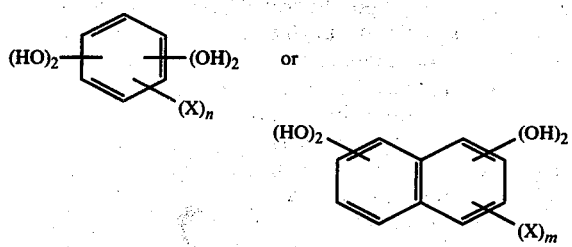

in which the OH groups in each pair are in positions ortho- to one another,

X represents a halogen atom, an OH group or a group of the formula R, OR or SR in which R represents a hydrocarbon or substituted hydrocarbon group, m represents 0, or an integer from 1 to 4, and n represents 0, 1 or 2.

Preferably m and n are 0, and the most preferred polyhydric phenol is 1,2,4,5-tetrahydroxy benzene. It is, however, possible to employ polyhydric phenols containing additional substituents. For instance, X can represent a group of the formula R, OR or SR in which R represents an alkyl, cycloalkyl, aryl, aralkyl or alkaryl group, which may be unsubstituted, or substituted by one or more halogen atoms.

A wide range of ketones, or dialkylacetals of such ketones can be employed in the process according to the invention. The ketone may, for example, have the formula $$R^1-CO-R^2$$

in which $R^1$ represents an alkyl, cycloalkyl, aryl, aralkyl or alkaryl group; and $R^2$ represents an alkyl, cycloalkyl, aryl, aralkyl or alkaryl group which may be unsubstituted or substituted on a carbon atom other than one adjacent to the carbonyl group, by a group of the formula $$-CO-R^1,$$

or $R^1$ and $R^2$ together with the carbonyl group to which they are attached represent the atoms necessary to complete a cycloaliphatic ketone or diketone.

The preferred ketones are acetone, hexan-2,5-dione, cyclohexan-1,4-dione or 1,4-diacetylbenzene. Acetone is the most preferred ketone. Where the ketone is a diketone, there is the possibility of polymer-formation with each of the carbonyl groups reacting with a different molecule of the polyhydric phenol. Acetyl acetone and other β-diketones cannot, however, be employed in the process according to the invention.

The preferred ketone acetal is the dimethyl acetal of acetone, i.e., 2,2-dimethoxypropane.

The process according to the invention is carried out in a non-aqueous solvent and in the presence of a strong Lewis acid catalyst. Examples of suitable catalysts are phosphorus pentoxide, toluene sulphonic acid, hydrochloric acid, sulphuric acid, boron trifluoride, zinc chloride and a aluminum chloride. The catalyst used depends largely on the ketone or ketone acetal, and it has been found that some Lewis acids are less effective catalysts than others. For example, the catalyst used for reaction of 2,2-dimethoxypropane with 1,2,4,5-tetrahydroxybenzene should be as strong a Lewis acid as possible. Preferably toluene sulphonic acid is used.

The choice of solvent that can be used in the process according to the invention is limited by the lack of solubility of many polyhydric alcohols in non-aqueous solvents. Examples of suitable solvents include tetrahydrofuran, dioxan dimethoxyethane, and diethylene glycol dimethyl ether. Where the ketone is acetone, it can also constitute the solvent, although only dilute solutions of the polyhydric phenols can be obtained in acetone. Reaction can be carried out at room temperature or at elevated temperature up to the boiling point of the solvent; for example, in diethylene glycol dimethyl ether, reaction can conveniently be carried out at a temperature of about 110° C. When a dialkyl acetal of the ketone is employed, the alcohol formed during the course of the reaction (methanol in the case of 2,2-dimethoxypropane) should be distilled off during the reaction to prevent it from interfering with the desired reaction.

Polymeric acetals, formed from diketones are of high heat stability.

The acetals formed by the process of the invention are of interest in perfumery. For example, 2,2,6,6-tetramethylbenzobisdioxole, the compound of Example 1 has an odour providing a green top note and may be employed in perfumes and fragrances to replace or supplement other materials possessing green top notes, such as phenyl acetaldehyde, hydrotropic aldehyde, acetals of these aldehydes, extract of violet leaves, galbanum oil, methyl heptine carbonate or methyl octine carbonate. Such materials will be well known to the perfume chemist, and details of such materials and formulations containing them are set out in such standard texts as "Chemistry and Manufacture of Cosmetics" by deNavarre (van Nostrand) and "Perfumes, Cosmetics and Soaps" by Poucher (Chapman and Hall).

The invention is further illustrated by the following Examples, in which the following abbreviations are employed:

THB: 1,2,4,5-tetrahydroxybenzene
THF: tetrahydrofuran
DMP: 2,2-dimethoxypropane
TsOH: p-toluene sulphonic acid
DGME: diethylene glycol dimethyl ether.

Example 1

THB (926g) and acetone (28.3 g) are dissolved in tetrahydrofuran (500 ml) in a flask protected from moisture by $CaCl_2$ tubes. Phosphorus pentoxide (84 g) is added to this mixture whereafter it is heated at 65° C. for 4 hours. The reaction mixture is allowed to cool, the liquid is decanted from the solid mass, and solid, dry potassium carbonate (5 g) is added. After stirring for 1 hour the liquid is decanted again and the solvent (THF) is distilled off leaving a brown solid residue. The latter is extracted with petroleum ether (100–200 ml) and filtered and the petroleum ether is distilled off. The residue is 2,2,6,6-tetramethyl-benzobisdioxole (11.5,g). Yield 28%. Mp after crystallization from petroleum ether: 120°–121° C. Infrared spectrum shows peaks at 6.7, 7.2, 8.0, 10.2 and 11.9μ. The 60 Mc proton NMR spectrum shows peaks at 1.6 ppm (H atoms of the methyl groups) and 6.2 ppm (aromatic H atoms). Elemental analysis:

C 65.0%, H 6.3%
$C_{12}H_{14}O_4$ requires C 64.8%, H 6.4%

Example 2

THB (10 g), Dimethoxypropane (14.8 g) and p-toluene sulphonic acid (0.025 g) are heated in THF (100 ml) for 120 hours. During the heating period a liquid of b.p. 60°–65° C. is distilled off through a distillation column and the volume in the flask is maintained at its original level by the addition of THF. In this way methanol is distilled off as it is formed.

A mixture of THF and methanol was distilled off during reaction (using a 60 cm Vigreux column) and the level in the flask was maintained by addition of THF. After 120 hrs. all DMP had disappeared. The solvent is then removed by distillation, the residue is dissolved in diethyl ether (100 ml) and washed with sodium hydroxide solution (2N, 100 ml). The two layers are separated, and the diethyl ether is distilled from the organic layer leaving 2,2,6,6-tetramethyl benzobisdioxole (5.3 g). Yield 34%. Mp after recrystallization from petroleum ether: 120°–121° C.

EXAMPLES 3 to 8

These were carried out in generally the same manner as Examples 1 and 2. The reactants, their amounts, the reaction conditions and the results are set out in the following Table.

TABLE

CONVERSION OF THB INTO 2,2,6,6-TETRAMETHYL BENZOBISDIOXOLE (BISACETAL)

| Example | THB g (mole) | Ketone component g (mole) | Condensing agent g (mole) | Solvent ml | Reaction Period | Reaction temp. °C | Bisacetal Yield % | Bisacetal mp °C |
|---|---|---|---|---|---|---|---|---|
| 3 | 5.8 (0.04) | Acetone, 5.9 (0.10) | $P_2O_5$, 14.0 (0.10) | THF, 100 | 30 min[1] | 65 | 12.4 | 120–121 |
| 4 | 10 (0.07) | Acetone, 10.1 (0.19) | $P_2O_5$, 30 (0.21) | THF, 200 | 4 hrs[2] | 65 | 25.5 | 115–119 |
| 5 | 5 (0.035) | Acetone, 10.1 (0.19) | $P_2O_5$, 15 (0.10) | THF, 100 | 90 min[3] | 20 | 9 | — |
| 6 | 10 (0.07) | 2,2-Dimeth.-xypropane (DMP), 14.8 | TsOH, 0.025 (0.001) | THF, 100 | 60 hrs[4] | 65 | 2.6 | — |
| 7 | 10 (0.07) | DMP, 14.8 (0.14) | TsOH 0.025 (0.001) | THF, 150 | 48 hrs[5] | 65 | 1.9 | — |
| 8 | 10 (0.07) | DMP, 125 ml (1) | TsOH, 0.025 (0.001) | DGME 50 | 90 hrs[6] | 110 | 17 | (6H) |

(1) After the heating period, the liquid phase is decanted from the $P_2O_5$, stirred for 1 hr. with dry, solid, $K_2CO_3$, and the solvent is distilled off. The residue is taken up on diethyl ether and extracted with 2-normal NaOH. The ether layer is dried over $Na_2SO_4$ and the solvent evaporated.

(2) The procedure is the same as in Example 3, except that after evaporation of the THF, the residue is extracted with warm petroleum ether. Upon standing the bisacetal crystallizes partly from the extract. More bisacetal is obtained by evaporation of the petroleum ether.

(3) The work-up is the same as in footnote (2).

(4) The distilling liquid was passed over CaH$_2$ (10 g) to remove methanol. After 6 hrs. all DMP has disappeared. The reaction mixture was worked up by distilling off the THF, dissolving the residue in diethyl ether and extracting with NaOH. The crude bisacetal was obtained from the ether layer. Also 50% of the THB was recovered.

(5) The distilling liquid was sent over solid NaOH (30 g) to remove methanol. After 48 hrs. DMP had completely disappeared. The reaction mixture was worked up as in footnote 4.

(6) DMP is used as the solvent but the THB only partially dissolves. After 48 hrs. heating 50 ml of DGME is added, causing complete solution of the THB. The work-up is as in former runs; the product is obtained as a dark oil.

EXAMPLES 9 to 13

Generally similar results were achieved by replacing the phosphorus pentoxide and toluene sulphonic acid used as catalyst/condensing agent with

| Example | Catalyst/Condensing Agent |
|---|---|
| 9 | hydrochloric acid |
| 10 | sulphuric acid |
| 11 | boron trifluride |
| 12 | zinc chloride |
| 13 | aluminium chloride |

EXAMPLES 14 and 15

Generally similar results were achieved by replacing the tetrahydrofuran and diethylene glycol dimethyl ether used as solvent with

| Example | Solvent |
|---|---|
| 14 | dioxan |
| 15 | dimethoxyethane |

EXAMPLE 16

A perfume composition with a floral bouquet suitable for use in cologne was produced having the following composition (the amounts given are all parts by weight).

| | |
|---|---|
| heliotropin | 2.0 |
| musk ambrette | 5.0 |
| p-cresyl acetate | 0.5 |
| p-cresyl phenylacetate | 1.5 |
| aldehyde C$_{14}$ | 1.0 |
| methylheptine carbonate 10% | 1.0 |
| methyl nonyl acetaldehyde | 1.0 |
| anisic aldehyde | 2.0 |
| styralyl acetate | 1.0 |
| phenyl acetaldehyde | 2.0 |
| 2,2,6,6-tetramethylbenzobisdioxole | 1.0 |
| oil bois de rose | 7.0 |
| oil ylang ylang extra | 5.0 |
| orangol | 5.0 |
| methyl anthranilate | 5.0 |
| alphine violet | 2.0 |
| hydroxy citronellol | 10.0 |
| jasmin nordene | 20.0 |
| benzyl acetate | 10.0 |
| geraniol extra | 8.0 |
| rhodinol | 10.0 |
| | 100.0 |

EXAMPLE 17

A parma violet fragrance suitable for incorporation in violet-scented perfumes and cosmetics was produced having the following composition (all parts are by weight).

| | |
|---|---|
| benzyl acetate | 100 |
| bergamol | 100 |
| methylheptine carbonate | 5 |
| 2,2,6,6-tetramethylbenzobisdioxole | 5 |
| orris conctric | 20 |
| methyl ionone | 500 |
| violet leaf absolute | 20 |
| ionone alpha | 150 |
| benzyl isoeugenol | 40 |
| ylang ylang | 20 |
| jasmine absolute | 20 |
| cassie absolute | 20 |
| | 1000 |

Obviously, many modifications and variations of the invention as hereinbefore set forth may be made without departing from the spirit and scope thereof. Therefore only such limitations should be imposed as are indicated in the following claims.

I claim:

1. As a novel compound, 2,2,6,6-tetramethyl-benzobisdioxole.

* * * * *